(12) United States Patent
Fischer et al.

(10) Patent No.: US 6,303,141 B1
(45) Date of Patent: Oct. 16, 2001

(54) TRANSDERMALLY ADMINISTRABLE MEDICAMENT WITH ACE INHIBITORS

(75) Inventors: Wilfried Fischer; Karin Klokkers; Anna Sendl-Lang, all of Holzkirchen (DE)

(73) Assignee: Hexal AG (DE)

( * ) Notice: Subject to any disclaimer, the term of this patent is extended or adjusted under 35 U.S.C. 154(b) by 0 days.

(21) Appl. No.: 09/407,348

(22) Filed: Sep. 29, 1999

Related U.S. Application Data

(63) Continuation of application No. 08/930,684, filed as application No. PCT/EP96/01402 on Mar. 29, 1996, now abandoned.

(30) Foreign Application Priority Data

Mar. 31, 1995 (DE) ............................................. 195 12 181

(51) Int. Cl.⁷ ................ A61K 9/70; A61K 9/14; A61R 13/00
(52) U.S. Cl. ................ 424/449; 424/443; 424/444; 424/445; 424/446; 424/447; 424/448
(58) Field of Search .............. 424/443, 447–448, 424/449

(56) References Cited

U.S. PATENT DOCUMENTS

| | | |
|---|---|---|
| 5,073,539 | 12/1991 | Mazzenga et al. . |
| 5,176,916 | 1/1993 | Yamanaka et al. . |
| 5,256,687 * | 10/1993 | Becker et al. .............. 514/419 |
| 5,269,875 | 12/1993 | Sonokawa et al. . |
| 5,464,387 * | 11/1995 | Haak et al. ................ 604/20 |
| 5,656,286 * | 8/1997 | Miranda et al. ............ 424/449 |

FOREIGN PATENT DOCUMENTS

| | | |
|---|---|---|
| 239074 | 7/1991 | (NZ) . |
| WO 93/23019 | 11/1993 | (WO) . |

* cited by examiner

Primary Examiner—Shelley A. Dodson
(74) Attorney, Agent, or Firm—Brooks & Kushman P.C.

(57) ABSTRACT

The invention relates to a transdermal system containing at least one angiotensin-converting enzyme inhibitor.

22 Claims, 1 Drawing Sheet

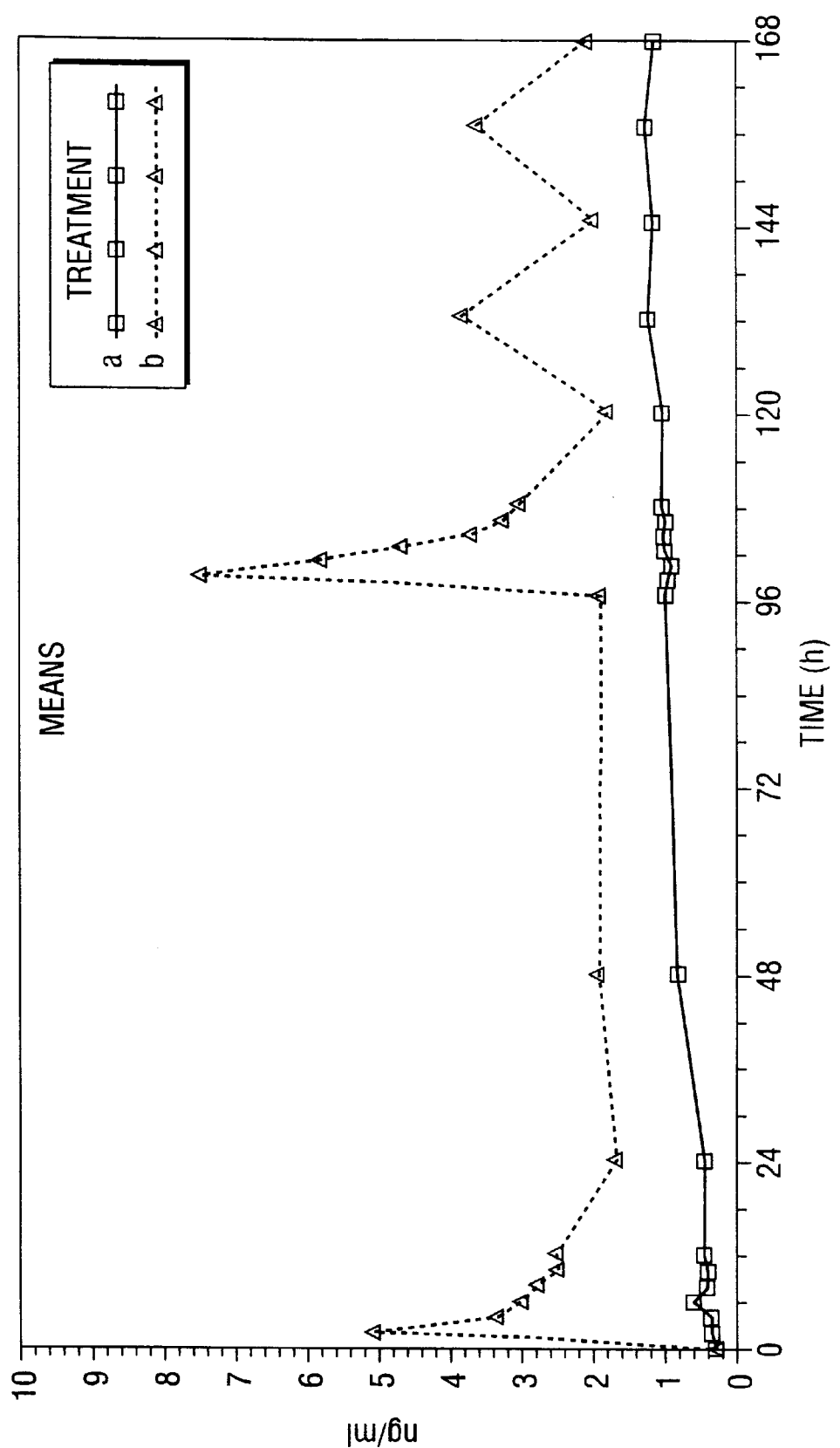

TRANSDERMALLY ADMINISTRABLE MEDICAMENT WITH ACE INHIBITORS

This is a continuation of application(s) Ser. No. 08/930,684 filed on Sep. 30, 1997 now abandoned which is a 371 of PCT/EP96/01402 filed Mar. 29, 1996.

The long-term therapy of hypertension with angiotensin-converting enzyme inhibitors (ACE inhibitors) has an increasingly wide scope. Together with good tolerability, ACE inhibitors are known for their reliable activity. The first substance of the ACE inhibitor class, captopril, is a very hydrophilic substance which is active in unmodified form. The oral bioavailability of captopril is approximately 70%. More recent ACE inhibitors, such as enalapril, are metabolized from their precursor during passage through the liver into the active component enalaprilate, that is to say the acid form. Like enalapril, the ACE inhibitors ramipril, cilacapril, trandolapril, benazepril or fosinopril are lipophilic prodrugs of the actual active form of the dicarboxylic acid. As a result of the esterification of one carboxyl group of the respective ACE inhibitor in each case, the substance becomes more lipophilic and thereby more favourable for oral absorption. The oral bioavailability of these prodrugs, however, is always lower than that of captopril. It is, for example, 28% for benazepril and about 40 to 60% for trandolapril. Now it is a known fact that substances having low bioavailability are very dependent on the respective metabolization capacity of the patients. This means that the resulting plasma levels are subject to a very high variation. The high variation in the blood levels of ACE inhibitors or their active forms leads, however, to uncertain courses of action. In order to make the action of ACE inhibitors independent of the metabolic condition of the patients, a pharmaceutical form which makes possible a reliable, reproducible systemic supply of the active compounds would be desirable. The transdermal administration of active compounds leads to a circumvention of the hepatic first-pass metabolism and thus to an elimination of the metabolization variations of the liver. If it was now possible to make ACE inhibitors in the form of their prodrugs or their active forms systemically available transdermally, a more reliable steady action could be achievable.

WO-A1-9 323 019 has already disclosed a transdermal reservoir system containing an ACE inhibitor and
(a) an impermeable covering layer (backing layer),
(b) a layer-like element having a hollow space,
(c) a means controlling the release of active compound (claim 1) and
(e) a covering layer (release liner) which can be torn off based on paper (page 12 lines 7/8).

Transdermal systems containing an ACE inhibitor are furthermore described in EP-A2-0 439 430 (reservoir TTS) and EP-A2-0 468 875 (matrix TTS), according to EP-A2-0 468 875 silicone elastomers being used as matrix material.

The object of the present invention is to provide a system for the transdermal supply of ACE inhibitors, in particular of ramipril, trandolapril and/or their therapeutically active salts, which is improved compared with the prior art.

In particular, it is an object of the invention to provide a system for the transdermal supply of ACE inhibitors, with which an activity of up to approximately one week can be achieved, such that for approximately one week a continuous release of active compound and a therapeutically effective plasma level can be achieved, for example of more than 0.5 ng of trandolapril/ml.

To do this, according to the invention a transdermal system having a matrix based on polyisobutylene or butyl rubber and containing at least one ACE inhibitor is provided. According to the invention, it was surprisingly found that lipophilic ACE inhibitors or their active forms, which can only permeate the human skin with difficulty, can penetrate the skin easily with the aid of a transdermally administrable medicament having a polyisobutylene matrix or butyl rubber matrix and produce a reliable, continuous blood level.

According to the invention, a release rate of the active compound from, for example, a polymer matrix, of 0.01 to 0.1 mg of active compound/$cm^2$ of 24 h and, in particular, 0.025 to 0.050 mg of active compound/$cm^2$ of 24 h can be achieved, such that a transdermal system according to the invention offers a plasma concentration of active compound in a therapeutically active amount. For example, for trandolapril a therapeutically active concentration in the blood of more than approximately 0.5 ng/ml can be achieved.

The person skilled in the art is familiar with suitable polyisobutylene or butyl rubber matrices; cf., for example, Higgins et al. in Satas, Handbook of Pressure Sensitive Adhesive Technology, 14:374 etc., Butyl Rubber and Polyisobutylene; Van Nostrand Reinhold, New York.

In the transdermal system according to the invention, the ACE inhibitor can be present in a concentration of at least 5% by weight and in particular in a concentration of 10 to 20% by weight (based on the matrix).

The ACE inhibitor can be employed here as a prodrug or as an active form.

Examples of ACE inhibitors which may be mentioned are ramipril, trandolapril and/or their active forms (acid forms) and also their therapeutically active salts.

The transdermal system according to the invention can include a permeation promoter, for example 2-octyldodecanol (Eutanol G).

Different forms of the transdermal systems according to the invention can be used, for example membrane- or matrix-controlled systems.

Thus, the transdermal system according to the invention can be a patch having a reservoir (patch of the reservoir type).

According to a specific embodiment, a patch of this type having a reservoir can be characterized by
(a) an impermeable covering layer (backing foil),
(b) a layer-like element having a hollow space,
(c) a microporous or semi-permeable membrane,
(d) a self-adhesive layer (adhesive layer) and
(e) if appropriate a covering layer (release liner) which can be torn off.

In this case, the layer-like element having a hollow space can be formed by the covering layer and the membrane.

The microporous or semi-permeable membrane can consist of an inert polymer, for example polypropylene, polyvinyl acetate or silicone.

According to a further specific embodiment of the invention the patch of the reservoir type can be characterized by
(a) an impermeable covering layer (backing foil),
(b) an open-pore foam, a closed-pore foam, a fabric-like layer or a web-like layer as a reservoir,
(c) if the layer according to (b) is not self-adhesive, a self-adhesive layer (adhesive layer) and
(d) if appropriate a covering layer (release liner) which can be torn off.

The reservoir can thus be formed, for example by a hollow space or in another manner. The reservoir is in this case filled with the active compound/mixture of the auxiliaries. For accommodating the active compound in the reservoir, reference may be made to the prior art for reservoir systems. After tearing off the covering film (protective film) and sticking the patch on the skin, the active compound with the auxiliaries permeates (through the membrane provided if appropriate) through the covering layer into the skin.

If a membrane is provided, depending on the pore width, it can have an action controlling the release of the active compound or alternatively no influence on the release of active compound from the system.

If the reservoir is provided by an open-pore foam, a closed-pore foam, a fabric-like layer or a web-like layer, the active compound/mixture of the auxiliaries are present in absorbed or finely divided form. In this case, a microporous or semi-permeable membrane can be absent, and the layer forming the reservoir can be self-adhesive or (if that is not the case) can carry a self-adhesive layer (adhesive layer).

According to a specific embodiment, the transdermal system according to the invention can be characterized by
(a) an impermeable covering layer (backing foil),
(b) a matrix layer for the active compound,
(c) (if the layer according to (b) is not self-adhesive) an active compound-permeable contact adhesive layer and
(d) if appropriate a covering layer (release liner) which can be torn off.

The matrix used according to the invention can be a self-adhesive polyisobutylene adhesive.

The invention is illustrated in greater detail below by means of examples.

EXAMPLES 1 to 5

A transdermal therapeutic system (TTS) of the matrix type is provided which is characterized, for example, by the following composition.

| Matrix: | Polyisobutylene adhesive (MA24 from Adhesive Research Inc., Glen Rock, Pennsylvania, USA) | |
|---|---|---|
| Covering film: | Polyester film (Hostaphan RN 19) | |
| Tear-off film: | Polyester film (Gelroflex PET 75 µm 1-S) or coated paper film (Gelrolease 603/100 DRS) | |
| Matrix constituents: | Trandolapril | 10% by weight |
| | Eutanol G | 5% by weight |
| | Polyisobutylene adhesive (Dry matter) | 85% by weight |

Comparison Example 1

Here, instead of a polyisobutylene adhesive, a silicone adhesive (BIO PSA X7 4302) is used.

The results obtained can be seen from the following Table.

A comparison of Example 1 and Comparison Example 1 shows that the active compound delivery in the system according to the invention remains constant over a period of 20 days, while it falls drastically in Comparison Example 1.

Use Example 1

In an in-vivo comparison study of a TTS according to the invention using an oral dose of trandolapril (capsule), the pharmacokinetic behaviour for TTS administration was tested on 6 healthy subjects. In this study, in the open 2-period cross-over design the TTS were administered over a period of 7 days (1 TTS for 4 days, then 1 TTS for 3 days) and, in comparison, 1 capsule of 2 mg of trandolapril was administered daily for 7 days. Blood samples were taken after the following times: −0.5; 0; 2; 4; 6; 8; 10; 12; 24; 48; 72; 96; 98; 100; 102; 104; 106; 108; 120; 132; 144; 156; 168 h after administration.

The pharmacokinetic results show that the TTS has a fundamentally different blood level profile than the capsules. In contrast to the capsule, a blood level which is constant over the respective administration period of 3 or 4 days is achieved, which is therapeutically also desirable. After oral administration, the blood concentration rises rapidly, in fact about 5 ng/ml is achieved within 2 h. Elimination takes place with a half-life of about 24 h. In comparison to this, the blood level course after TTS administration is more uniform. In the first 4 days of use, a uniform slight rise in the blood level of about 0.3 ng/ml after 6 h to about 1 ng/ml after 96 h is to be observed. After changing the TTS after 96 h, the blood levels in the second administration period only rise insignificantly (FIG. 1). Thus the blood level profile after administration of the TTS comes very close to the therapeutic ideal of constant blood levels during treatment. Undesired blood level peaks, which can be associated with undesired side-effects such as sudden blood pressure drop, are safely avoided.

| | | | | Release of active compound [mg/cm$^2$] | | | |
|---|---|---|---|---|---|---|---|
| Example | Adhesive | Active compound: trandolapril [%] | Permeation promoter [%] | Day from preparation | Skin permeation [24 h] | Diss. [6 h] | Crystallization |
| E 1 | Polyisobutylene | 3 | 0 | 4 | 0.013 | | none |
| | | | | 7 | | 0.008 | |
| | | | | 20 | | 0.008 | |
| E 2 | | 5 | 0 | 4 | 0.014 | | none |
| | | | | 7 | | 0.009 | |
| | | | | 20 | | 0.011 | |
| E 3 | | 10 | 0 | 4 | 0.027 | | none |
| | | | | 7 | | 0.019 | |
| | | | | 20 | | 0.019 | |
| | | | | 37 | 0.023 | | |
| E 4 | | 10 | 10 Citiol V | 13 | 0.044 | | none |
| E 5 | | 10 | 5 Eutanol G | 8 | 0.061 | | none |
| CE 1 | Silicone | 3 | 0 | 0 | 0.065 | | none |
| | | | | 15 | 0.030 | | none |
| | | | | 26 | | 0.076 | |
| | | | | 33 | 0.017 | | |

What is claimed is:

1. A passive sustained release transdermal drug delivery system, comprising:
a matrix comprising polyisobutylene, butylene rubber, or mixtures thereof, and an angiotensin-converting enzyme inhibitor which comprises at least one of ramipril or trandolapril.

2. The transdermal drug delivery system of claim 1 wherein said angiotensin-converting enzyme is present in a concentration of at least about 5 weight percent based on the weight of said matrix.

3. The transdermal drug delivery system of claim 1 wherein said angiotensin-converting enzyme is present in an amount 10 from about 10 weight percent to about 20 weight percent based on the weight of said matrix.

4. The transdermal drug delivery system of claim 1 wherein said angiotensin-converting enzyme is present in the form of a prodrug.

5. The transdermal drug delivery system of claim 1 wherein said angiotensin-converting enzyme is present in an active form.

6. The transdermal drug delivery system of claim 1, wherein said matrix further comprises a permeation promoter.

7. The transdermal drug delivery system of claim 6 wherein said permeation promoter comprises 2-octyldodecanol.

8. The transdermal drug delivery system of claim 1, wherein said transdermal drug delivery system comprises a patch suitable for adhering to the skin, said patch having a matrix-containing reservoir.

9. The transdermal drug delivery system of claim 8, wherein said patch comprises
   (a) an impermeable covering layer;
   (b) a layer element having a hollow space;
   (c) a microporous or semi-permeable membrane;
   (d) an adhesive layer; and
   (e) optionally a release liner.

10. The transdermal drug delivery system of claim 8, wherein said reservoir is formed by a hollow space between said covering layer and said membrane.

11. The transdermal drug delivery system of claim 9 wherein said membrane comprises an inert polymer.

12. The transdermal drug delivery system of claim 11 wherein said inert polymer is selected from the group consisting of polypropylene, polyvinylacetate, silicone, and mixtures thereof.

13. The transdermal drug delivery system of claim 8 wherein said reservoir comprises an open-pore foam, a closed-pore foam, a fabric layer, or a web layer.

14. The transdermal drug delivery system of claim 8 wherein said matrix is self-adhesive.

15. The transdermal drug delivery system of claim 7 wherein said matrix is self-adhesive.

16. A transdermal drug delivery system, comprising:
   (a) an impermeable covering layer;
   (b) a matrix according to claim 1, said matrix being self-adhesive;
   (c) optionally, a removable release liner superficial to said matrix.

17. The transdermal drug delivery system of claim 9 wherein said release liner comprises one or more polymers selected from the group consisting of polyester, polypropylene, and paper coated with a release coating of silicone or polyethylene.

18. The transdermal drug delivery system of claim 16 wherein said release liner comprises one or more polymers selected from the group consisting of polyester, polypropylene, and paper coated with a release coating of silicone or polyethylene.

19. The transdermal drug delivery system of claim 9 wherein said covering layer comprises one or more polymers selected from the group consisting of polyester, polypropylene, polyethylene, and polyurethane.

20. The transdermal drug delivery system of claim 16 wherein said covering layer comprises one or more polymers selected from the group consisting of polyester, polypropylene, polyethylene, and polyurethane.

21. A passive transdermal drug delivery system comprising:
   a) an impermeable covering layer;
   (b) an active-substance-containing matrix layer; and
   (c) optionally, a removable release liner,
   wherein the active substance in said active-substance-containing layer comprises a prodrug form or active form of at least one angiotensin-converting enzyme selected from the group consisting of ramipril and trandolapril; optionally a permeation promotor; and a matrix polymer selected from the group consisting of polyisobutylene, butyl rubber, and mixtures thereof, said angiotensin-converting enzymes present in said active substance-containing matrix layer in an amount of from about 10 weight percent to about 20 weight percent based on the weight of said active substance-containing matrix layer.

22. A method for the passive sustained release administration of an active or prodrug form of an angiotensin-converting enzyme selected from ramipril, trandolipril, or mixtures thereof to a patient in need of same, said method comprising contacting the skin of said patient with a sustained release matrix comprising a carrier selected from the group consisting of polyisobutylene, butylene rubber, and mixtures thereof, said matrix containing in excess of 5 weight percent of said angiotensin-converting enzyme based on the weight of said matrix.

* * * * *